(12) United States Patent
Guillen (10) Patent No.: US 6,371,931 B1
(45) Date of Patent: Apr. 16, 2002

(54) REFLEX TESTER AND METHOD FOR MEASUREMENT OF RANGE OF MOTION AND PERIPHERAL VISION

(76) Inventor: Diego Guillen, 805 E. Mobeck #A, West Covina, CA (US) 91790

( * ) Notice: Subject to any disclaimer, the term of this patent is extended or adjusted under 35 U.S.C. 154(b) by 0 days.

(21) Appl. No.: 09/492,855

(22) Filed: Jan. 27, 2000

Related U.S. Application Data

(62) Division of application No. 09/060,261, filed on Apr. 15, 1998, now Pat. No. 6,066,105.

(51) Int. Cl.⁷ .................................................. A61B 5/00
(52) U.S. Cl. ........................................ 600/595; 273/445
(58) Field of Search ................................. 600/587, 595; 273/445, 446; 434/258; 351/203

(56) References Cited

U.S. PATENT DOCUMENTS

| | | | | |
|---|---|---|---|---|
| 4,063,807 A | * | 12/1977 | Gelius et al. | 351/226 |
| 4,261,563 A | * | 4/1981 | Goldfarb | 463/7 |
| 4,824,237 A | * | 4/1989 | Ratner et al. | 351/203 |
| 5,079,726 A | * | 1/1992 | Keller | 702/142 |
| 5,203,346 A | * | 4/1993 | Fuhr et al. | 600/594 |
| 5,221,243 A | * | 6/1993 | Walker | 482/83 |
| 5,490,517 A | * | 2/1996 | Whitman et al. | 600/587 |
| 5,520,393 A | * | 5/1996 | Rickey, Jr. | 273/237 |
| 5,803,745 A | * | 9/1998 | Kozak et al. | 434/236 |
| 5,812,239 A | * | 9/1998 | Eger | 351/203 |
| 5,882,011 A | * | 3/1999 | Praria | 273/445 |

\* cited by examiner

Primary Examiner—John P. Lacyk
Assistant Examiner—Charles Marmor, II (57) ABSTRACT

A response measuring system for measuring the time required for a user or patient to respond to a prompting event includes a controller or computer connected to a plurality of annunciator driving outputs and a plurality of sensor input receivers. The controller also includes a timer responsive to both annunciator driving outputs and sensor input receivers; a controller memory stores response times. The annunciators can be lights or tactile vibrating stimulators for cuing or prompting the user into responding. The sensors, in general terms, sense the user's response and the timer is used to measure the interval required for the user to respond. The system includes a support member or housing for carrying and positioning the sensors and annunciators for a given experiment. In a first embodiment of the reflex measuring system of the present invention, a housing includes a first and second areas adapted to receive left and right hands with subareas designated for each finger, each with a vibrotactile stimulator, a button actuated microswitch (or reset button) and, preferably, just beyond each finger subarea, a light emitting diode (LED) visibly positioned for indicating which finger is to be flexed in responding to the stimulus. The stimulus is either actuation of the selected LED light source, actuation of the selected vibrotactile stimulator, or both. Once the user sees the LED or feels the vibrotactile stimulator actuated under a selected finger, the user immediately depresses the appropriate reset button. The controller then senses the amount of time elapsed between actuation of the selected light indicator (or vibrotactile annunciator) and sensing of the user's correct response. After test completion, the reaction times may be plotted to show the results.

10 Claims, 10 Drawing Sheets

REFLEX TESTER AND METHOD FOR MEASUREMENT OF RANGE OF MOTION AND PERIPHERAL VISION

This application is a divisional application of application Ser. No. 09/060,261, filed Apr. 15, 1998 (now U.S. Pat. No. 6,066,105), the entire disclosure of which is incorported herein by reference.

BACKGROUND OF THE INVENTION

1. Field of the Invention

The present invention relates to a system and method for testing reflexes, reaction time and range of mobility for patients or users and, more particularly, to a system for automated testing and data recording for use by physicians, physical therapists and trainers.

2. Discussion of the Prior Art

A number of reaction testing devices have been employed in games for amusement and for diagnostic testing of physical acuity, reaction time and dexterity.

NASA has used reaction testing for measurement of "simple" and "disjunctive" responses to light stimuli, as disclosed in U.S. Pat. No. 3,698,385, to Low et al., in which a base includes two parallel finger grooves with sensors. The subject observes "ready", "left" and "right" light indicators and responds by placing a finger in a selected groove where the finger's presence is sensed, a test which provides a raw count of the number of clock cycles required for a given individual to correctly respond to the "left" or "right" light stimulus.

Others have used systems with similar electrical circuits to provide specific kinds of occupational training (see, e.g., U.S. Pat. No. 4,589,849 to Casey and U.S. Pat. No. 5,289,389 to Keller), and dancing (as shown in U.S. Pat. No. 3,233,341). But none of these devices is readily used in a comprehensive regimen of physical therapy for testing a patient's reflexes and/or range of mobility. A physician, physical therapist, trainer, or occupational therapist requires a way to provide a meaningful examination of a patient's capabilities and to determine how the patient's capabilities are changing as therapy progresses.

OBJECTS AND SUMMARY OF THE INVENTION

Accordingly, it is an object of the present invention to measure, store and display the reaction time required for a patient to touch, press or manipulate an object at an indicated location.

It is also an object of the present invention to measure, store and display the reaction time required for a patient to move a selected object from a first indicated location to a second indicated location.

Another object of the present invention is measuring the range of motion for the patient's shoulders, arms, fingers, feet, ankles, knees, hips and back.

Another object of the present invention is to store and display trend data on the improvement, or lack thereof, for a given patient's reflexes, reaction time, dexterity, eye-hand coordination, and range of motion, over a course of therapy.

The aforesaid objects are achieved individually and in combination, and it is not intended that the present invention be construed as requiring two or more of the objects to be combined unless expressly required by the claims attached hereto.

In accordance with the present invention, a response measuring system for measuring the time required for a user (e.g., a patient) to respond to a prompting event includes a controller or computer connected to a plurality of annunciator driving outputs and a plurality of sensor input receivers. The controller also includes a timer responsive to both annunciator driving outputs and sensor input receivers; a controller memory stores response times. The annunciators can be lights or tactile vibrating stimulators for cuing or prompting the user into responding. The sensors, in general terms, sense the user's response and the timer is used to measure the interval required for the user to respond. The system includes a support member or housing for carrying and positioning the sensors and annunciators for a given experiment.

In a first embodiment of the reflex measuring system of the present invention, a housing includes a first area adapted to receive a left hand and, optionally, a second area adapted to receive a right hand; subareas are designated for each finger. The finger subareas in the first and second areas each include a vibrotactile stimulator, a button actuated microswitch (or reset button) and, preferably, just beyond each finger subarea, a light emitting diode (LED) or other light source visibly positioned for indicating which finger is to be flexed and depressed in responding to the stimulus. The stimulus comprises actuation of the selected LED light source, actuation of the selected vibrotactile stimulator, or both. Once the user sees the LED or feels the vibrotactile stimulator actuated under a selected finger, the user immediately depresses the appropriate reset button. The controller then senses the amount of time elapsed between actuation of the selected light indicator (or vibrotactile annunciator) and sensing of the user's correct response. A test pattern (for recording) or an exercise pattern (not to be recorded) may be performed and testing can be divided into two areas. The patient can be tested to determine whether response is faster for what is seen (e.g., the LED) or what is felt (e.g., the vibrotactile stimulator). The timer (or clock) is activated immediately upon lighting of the LED indicator or activating of the finger vibrotactile stimulator and is stopped upon pressing of the indicated reset button. After completion of the test, the reaction time measurements may be plotted to show the results using the computer display or an attached printer.

In a second embodiment, a vertical panel includes a plurality of pegs of various readily distinguishable sizes and shapes are arranged in a plurality of columns to the left and right of a central area. Alternatively, the panel can lie in a horizontal orientation or can be adjustably tilted to a selected angle. The number of columns and pegs per column are selectable to satisfy the requirements of a given application, and preferably, the pegs are color coded. Preferably, on the left, first, second and third columns each contain seven shapes stored within vertically arrayed pockets; the shapes can be, for example, a small circle, a large circle, a rectangle, a diamond, a triangle, a square and a star. Each shape is a "peg" or test object which can be removed from a holder or pocket in selected one of the columns and placed in a specified corresponding receiving aperture (having the same shape and, preferably, color) within the central area. Each receiving aperture includes an annunciator or indicator (e.g., an LED) and a sensor to detect the presence of the test object. Preferably, three columns are arranged to one side (e.g., the left) of the central area with three columns arranged to the opposing side (e.g., the right), thereby allowing the user to demonstrate a range of motion in reaching outwardly, to opposing sides (e.g., left or right), to the outer columns, as well as reaching up or down, within a column. In use, the selected test object is illuminated using an LED annunciator, thereby starting the timer. The user or patient immediately grasps the test object and removes it from the holder in the starting column, moves the object and then inserts it into a corresponding indicated aperture in the central area, thereby triggering a sensor in the receiving aperture. The timer measures the time required for the patient to complete the operation.

The peg board includes an instruction display for displaying the message "move star from left bank column 2, to lighted star position in center bank" (citing a single example). The time required for the patient to perform this operation is measured and recorded; in addition, the system measures and records how long the message was displayed and the time used for the user to return the 'test hand' back to the starting position. Preferably, results for a minimum of three trials are recorded. The system also has the capability of running a test pattern and a random practice or exercise pattern.

In a third embodiment, the system includes a housing having a substantially hemispherical interior surface preferably including several dozen lighted buttons. The hemispherical system is intended for use in therapeutic centers as well as athletic training facilities. Each lighted button includes an annunciator light and a sensor microswitch for generating a sensor input signal. Preferably, the lighted buttons are arrayed in radial lines within the hemispherical surface. A first, large, lighted button is disposed approximately at the center of the hemisphere, preferably at the intersection of two perpendicular lines bisecting the hemisphere. In the exemplary embodiment, a first circular array of twelve small, equally spaced lighted buttons encircles the central lighted button at a first radius. The first circular array of lighted buttons corresponds roughly to the positions of the numerals on an analog clock face. Preferably, six more circles of twelve lighted buttons each are arranged at radii progressively larger than the first radius, thereby providing twelve linear, radially projecting arrays of seven lighted buttons each, the buttons are spaced evenly in radius to the edge of the hemispherical interior surface. If seven or more circles of lighted buttons are provided, greater resolution in characterizing the user's range of motion (and visual acuity) is obtained.

The hemisphere is defined in four quadrants, the first quadrant begins at position one and extends through position three (including three radial arrays of small buttons). The second quadrant begins at position four and extends through position six (also including three radial arrays of small buttons). The third quadrant begins at position seven and extends through position nine and the fourth quadrant begins at position ten and extends through position twelve. The four quadrants are arrayed to cover a 360° circle within the hemispherical surface.

In use, a user stands at approximately the center of the hemisphere and places an extremity (e.g. a hand) on the central lighted button, thereby activating the system and indicating that the user is ready to begin, whereupon a test or exercise pattern of light illumination is commenced. During the test, the user begins with the hands at rest and one of the smaller lighted buttons (e.g., at radial row three, position five) is illuminated (thus becoming an 'object button'); the user immediately depresses the object button and then reaches back to touch the central lighted button, thus indicating an end to a test move. The controller timer measures the time taken for each step. In the present example, when the fifth reset light located on row 3 is lit, the controller immediately actuates (e.g., turns on) a first timer, thus measuring time required for the user to press the reset (or object) button located on row 3 position 5. Immediately upon pressing reset button on row 3 position 5, a second timer is actuated for measuring time required to press the reset button located in the center. The times required for the user to perform the indicated operations are thereby measured and recorded in a procedure allowing measurement of a user's accuracy, speed and range of motion (e.g., for hands, feet, elbows, knees, etc.), as observed from performing the task of identifying and pressing the object button and then pressing the center reset button.

An important feature of the controller in the present invention is that several sets of test results can be stored and date-stamped so that the therapist or physician can analyze a patient's progress over time by analyzing the trends in reaction time for selected stimuli. The data can be organized by test type and by the specific stimulus presented to the patient.

The computer or controller includes software for analyzing and displaying the data in any of several formats. The data can be moved to a spreadsheet or database for storage, plotting and printing. The computer software allows the therapist to either perform a test (or exercise), archive patient histories, or display the patient histories, and prepare written documents, as necessary. If performing a test is chosen from the initial menu, the first step is to prompt for test configuration and patient information, then check and hold for patient ready condition, perform the test and display the results, record the results, and display the results with analysis. The initial prompt gives the therapist an opportunity to record information needed to perform the test or exercise and provide identifying information about the patient such as the patient name and other vital information. The therapist also selects whether to use a random sequence of a selected length or a preselected sequence and whether results should be recorded (for a test) or not recorded (for an exercise).

Initially, the user or patient must be readied for the test whereby the hand placement is checked and sensors are checked for activation, in sequence. Once the appropriate sensors are activated, a waiting period of approximately 10 seconds passes and the patient is deemed to be ready. In performing the test, the software directs the system to light one of the finger lights and time the interval between the light coming on and the appropriate button being pressed. Once the test sequence is completed using light annunciators, the test is repeated using the vibrotactile buzzer annunciators. If an error occurs during testing (such as the wrong finger button being pressed) the error is recorded along with other test results.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

DESCRIPTION OF THE PREFERRED EMBODIMENT

Figure 1:
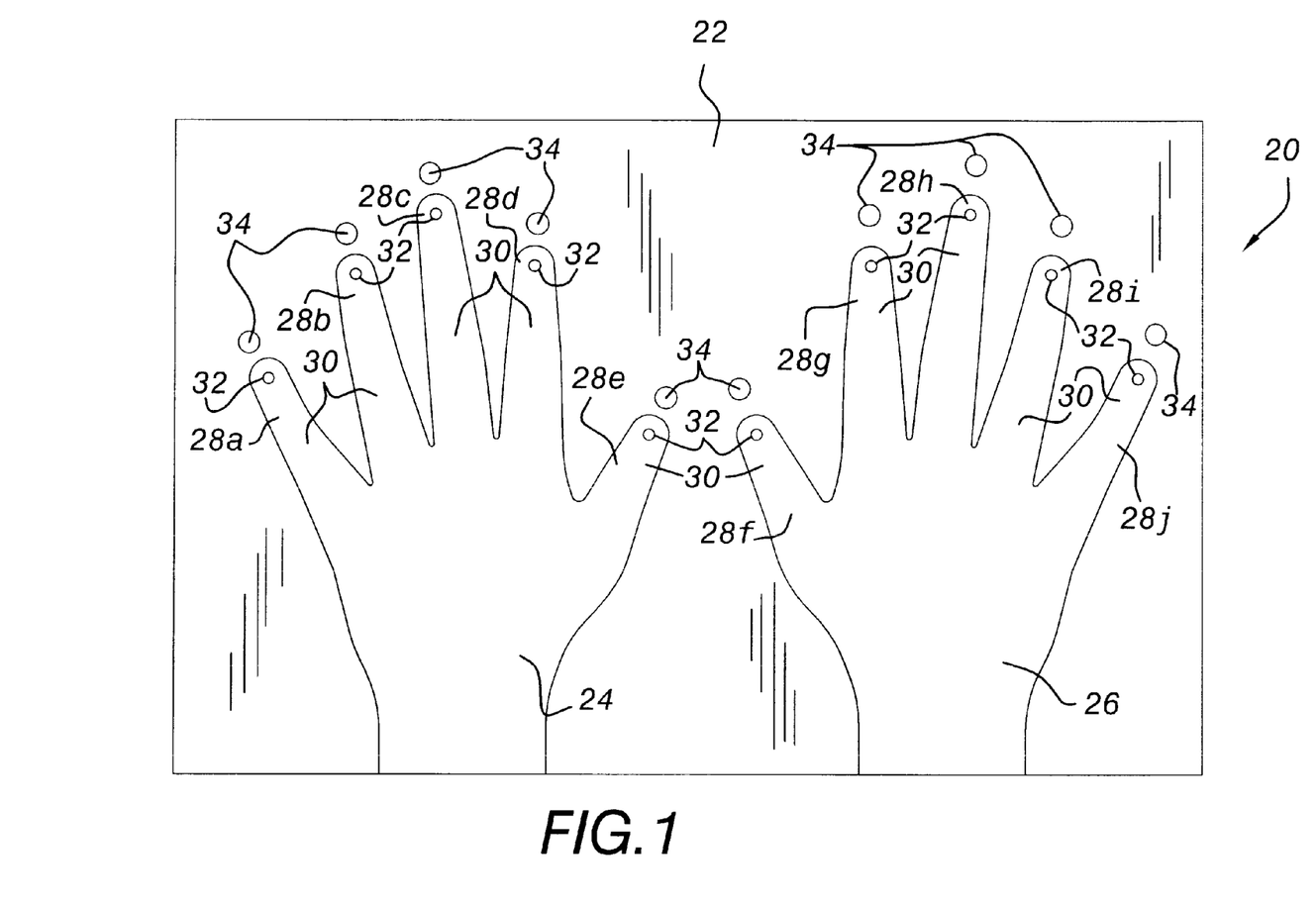
FIG. 1 is a top view of a response measuring system housing including a first area adapted to receive the left hand and a second area adapted to receive the right hand.

Referring specifically to FIG. 1 of the accompanying drawings, a reflex tester or response time measuring system 20 includes a housing 22 having an upper surface including a left hand area 24 and a right hand area 26, adapted to receive the user's left and right hands, respectively. Housing 22 may optionally include only a single hand receiving area (e.g., 24 or 26), in a range of sizes for users of differing hand size or shape, or in a range of finger/thumb orientations. Finger subareas 28a–28j are designated for each finger and thumb in hand areas 24, 26. The finger subareas 28a14 28e in the first, left hand area 24 and finger subareas 28f–28j in second, right hand area 26 each include a vibrotactile stimulator 30 (located within the housing at approximately the mid-point of each finger subarea 28a–28j), a button actuated microswitch (or reset button) 32 located under the finger-pad area near the finger subarea distal end and, preferably, just beyond each finger subarea 28a–28j, a light emitting diode (LED) 34 or other light source visibly positioned for indicating which finger is to be flexed in responding to the selected stimulus. The stimulus comprises actuation of the selected LED light source 34, actuation of the selected vibrotactile stimulator 30, or both. Once the user sees actuation of a selected LED 34 (e.g., for finger subarea 28e under the left thumb) or feels the vibrotactile stimulator 30 actuated, the user immediately depresses the appropriate reset button 32. A computer or controller (not shown) then senses the amount of time elapsed between actuation of the selected light indicator 34 (or vibrotactile annunciator 30) and sensing of depression of the button 32 signaling the user's correct response. A test pattern (for recording) or an exercise pattern (not recorded) may be performed and testing can be divided into two areas. The patient can be tested to determine whether response is faster for what is seen (e.g., the LED 34) or what is felt (e.g., the vibrotactile stimulator 30). The controller timer (or clock) is activated immediately upon lighting of the LED indicator 34 or activating of the finger vibrotactile stimulator 30 and is stopped upon pressing of the indicated, corresponding reset button 32. After completion of the test, the reaction time measurements may be plotted to show the results using the computer display or an attached printer.

In general, response measuring system 20 measures the time required for a user (e.g., a patient) to respond to a prompting event and includes a controller or computer (not shown) connected to a plurality of annunciator driving outputs and a plurality of sensor input receivers. The controller also includes a timer responsive to both annunciator driving outputs and sensor input receivers; a controller memory stores response times. The annunciators can be lights or tactile vibrating stimulators for cuing or prompting the user into responding. The sensors, sense the user's response and the timer is used to measure the interval required for the user to respond. The system includes a support member (e.g., housing 22) for carrying and positioning the sensors and annunciators for a given experiment.

Figure 2:
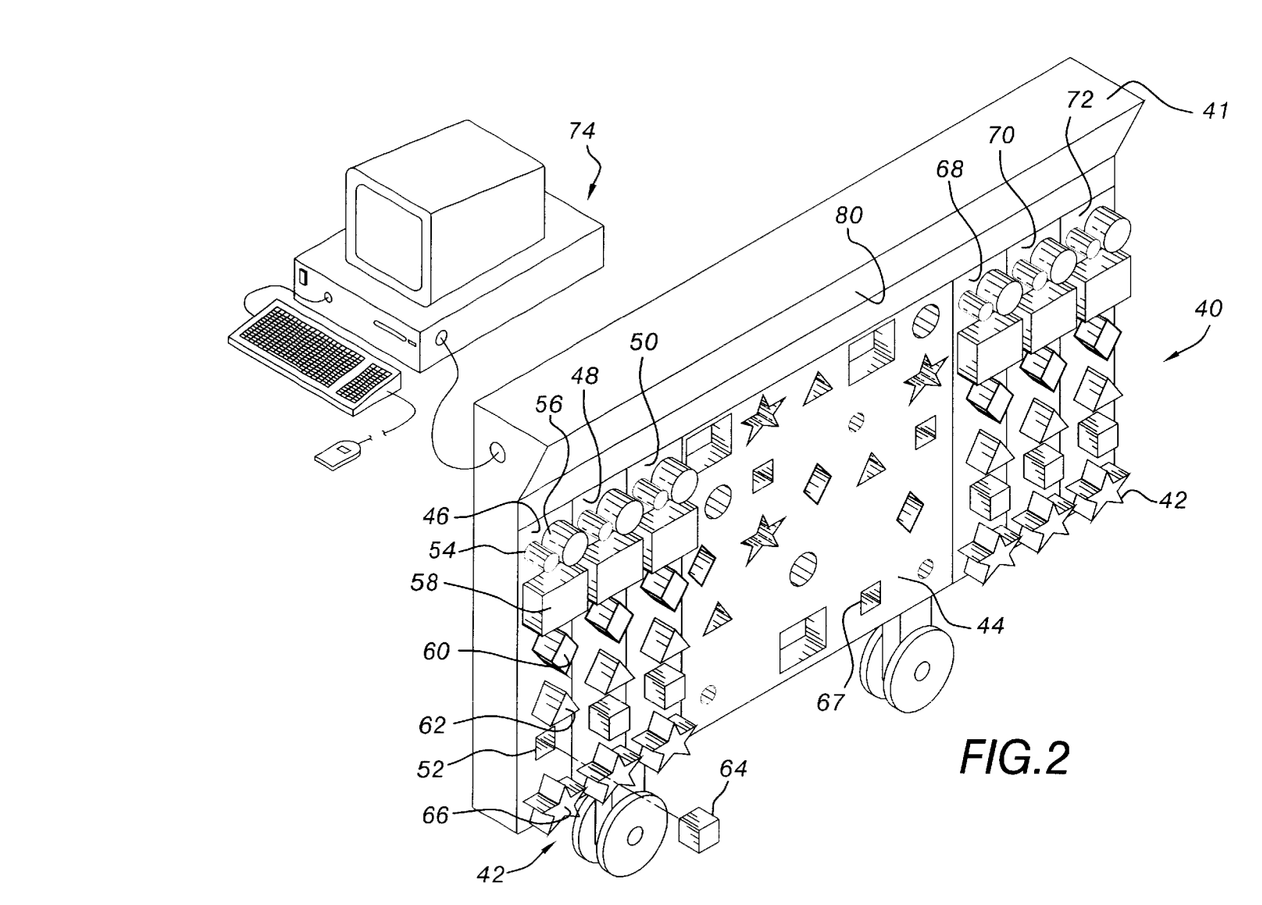
FIG. 2 is a perspective illustration of a reflex measuring system including a plurality of test objects.

In a second embodiment, as best seen in FIG. 2 a reflex measuring system 40 includes a vertically oriented panel housing 41 with plurality of test objects or pegs 42 of various readily distinguishable shapes and sizes arranged in a plurality of columns to the left and right of a central area 44. Alternatively, panel housing 41 can lie in a horizontal orientation or can be adjustably tilted to a selected angle; panel housing 41 is preferably height adjustable and can be raised a selected distance from the floor and locked in a selected angular orientation and at a selected height. The number of columns and pegs per column are selectable to satisfy the requirements of a given application, and preferably, the pegs 42 are color coded. Preferably, on the left, first column 46, second column 48 and third column 50 each contain seven shaped pegs 42 stored within vertically arrayed pockets. 52. As shown in FIG. 2, each column (e.g., 46) includes pegs in the following shapes: a small circle peg 54, a large circle peg 56, a rectangle peg 58, a diamond peg 60, a triangle peg 62, a square peg 64 and a star peg 66. The peg shapes and quantities shown in FIG. 2 are exemplary only; many other shapes could be used and more or fewer shapes could be employed, further, in alternative embodiments, the shapes can be of uniform color.

In the embodiment of FIG. 2, each peg (e.g., 58) can be removed from a holder or pocket 52 in selected one of the columns (e.g., square peg 64) and placed in a corresponding receiving aperture (e.g., square aperture 67) within the central area 44; corresponding apertures within the central area 44 have the same cross-sectional shape and, preferably, color as the selected peg and are sized to slidably receive the corresponding peg. Each receiving aperture (e.g., 67) includes a sensor to detect the presence of the peg, once inserted, and a source of illumination selectively enabled and responsive to controller 74. Preferably, three columns 46, 48, 50 are arranged to the left of the central area 44 with three columns 68, 70, 72 arranged to the right, thereby. allowing the user to demonstrate a range of motion in reaching outwardly, left or right, to the outer columns 56, 72, as well as reaching up or down, within a column (for a selected panel housing height). The pegs 42 are preferably at least partially translucent and pass illumination provided from within pocket 52; an LED in each pocket 52 is selectively enabled and responsive to controller 74.

In use, the selected test object (e.g.,58) is illuminated using an LED annunciator situated within the pockets 52 (the LEDs are as described in the first embodiment, above), thereby starting a timer in controller or computer 74. The user or patient immediately grasps the peg 58 and removes it from the pocket holder in the starting column (e.g., 56), moves the peg 58 and then inserts it into corresponding receiving aperture 67 in central area 44, thereby triggering a sensor in the receiving aperture 67. The timer measures the time required for the patient to complete the operation.

Another exercise is performed to measure the time required to move all pegs from one or more side columns (e.g., left side first column 46) into corresponding apertures in central area 44. Alternatively, the exercise can be started with the pegs installed in the receiving apertures of central area 44 and the user is timed while moving all pegs to the appropriate pockets in one or more selected side columns (e.g., columns 48 and 50).

The peg board includes an instruction display 80 for displaying the message "move rectangle from left bank column 1, to lighted rectangle position in center bank" (citing a single example). The time required for the patient to perform this operation is measured and recorded; in addition, the system measures and records how long the message was displayed and the time used for the user to return the 'test hand' back to the starting position. Preferably, results for a minimum of three trials are recorded. The system also has the capability of running a test pattern and a random practice or exercise pattern.

Figure 3:
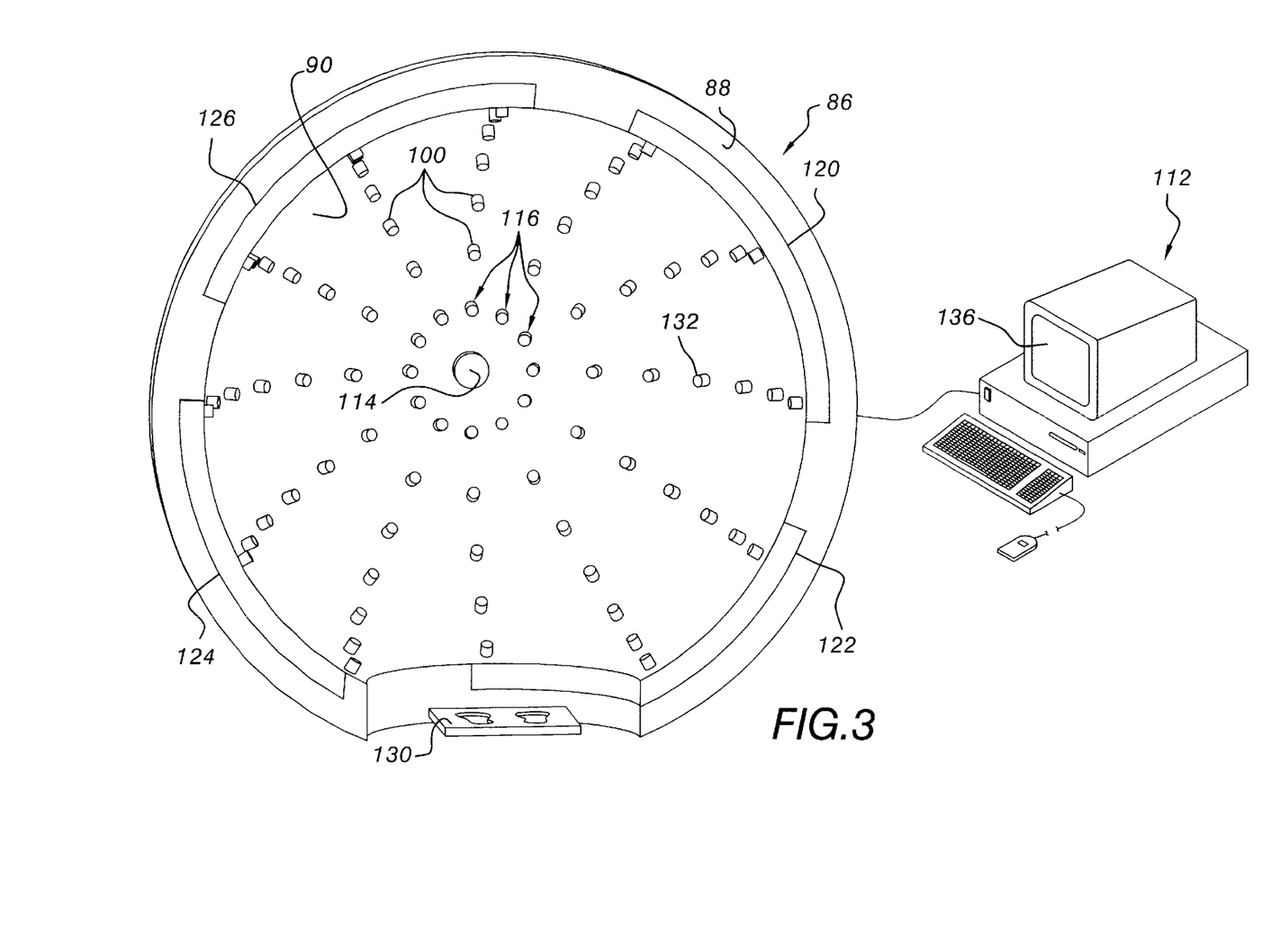
FIG. 3 is a perspective view of an hemispherical reflex testing system.

In a third embodiment, as best seen in FIG. 3, a hemispherical reflex testing system 86 includes a housing 88 having a substantially hemispherical interior surface 90 preferably including several dozen lighted button-actuated electrical switches 100.

The hemispherical system 86 is intended for use in therapeutic centers as well as athletic training facilities. Each lighted button 100 includes an annunciator light (or LED) and a sensor microswitch for generating a sensor input signal for transmission to a computer or controller 112 connected thereto. Preferably, the lighted buttons 100 are arrayed in radial lines within the hemispherical surface 90. A first, large, lighted reset button 114 is disposed approximately at the center of the hemisphere, at the intersection of two perpendicular lines bisecting the hemisphere. A first circular array 116 of twelve small, preferably equally spaced lighted buttons 100 encircles the central lighted button 114 at a first radius. The first circular array 116 of lighted buttons corresponds roughly to the positions of the numerals on an analog clock face. Six more circles of twelve lighted buttons each are arranged at radii progressively larger than the first radial array 116, thereby providing twelve linear, radially projecting lines of seven lighted buttons 100 each, the buttons 100 are spaced evenly in radius to the edge of the hemispherical interior surface 90. Alternatively, the buttons in first circular array 116 can be irregularly spaced, and more or fewer than twelve buttons can be included, and the remaining buttons 100 may be in a curved (as opposed to straight) line or may be irregularly or randomly positioned about the hemispherical interior surface 90.

Returning to the embodiment of FIG. 3, hemisphere surface 90 is defined in four quadrants, the first quadrant 120 begins at position one (i.e., with the one o'clock radial array) and extends clockwise through position three (including three radial arrays of small buttons 100). The second quadrant 122 begins at position four and extends clockwise through position six (also including three radial arrays of small buttons 100). The third quadrant 124 begins at position seven and extends clockwise through position nine and the fourth quadrant 126 begins at position ten and extends clockwise through position twelve (corresponding to the vertically aligned buttons at twelve o'clock). The four quadrants are arrayed to cover a 360° circle within the hemispherical surface 90. For purposes of nomenclature, button 132 is at position three, radius five, counting radially outwardly from center button 114, which is designated position zero.

In use, a user stands at a test position 130 (preferably including designated positions for left and right feet ) approximately the center of the hemisphere and places an extremity (e.g. a hand) on the central lighted button 114, thereby activating the system and indicating that the user is ready to begin, whereupon a test or exercise pattern of light illumination is commenced. During the test, the user begins with the hands at rest and one of the smaller lighted buttons (e.g., 132 at radial row three, position five) is illuminated (thus becoming an 'object button'); the user immediately depresses the object button 132 and then reaches back to touch the central lighted button 114, thus indicating an end to a test move. The controller 112 includes a timer for measuring the time taken for each step. In the present example, when the fifth reset light located on row position three is lit, the controller immediately actuates (e.g., turns on) a first timer, thus measuring time required for the user to press the object button 132. Immediately upon pressing button 132 (which is also deemed a reset button 132), a second timer is actuated for measuring time required to press the center reset button 114. The times required for the user to perform the indicated operations are thereby measured and recorded in a procedure allowing measurement of a user's accuracy, overall eye-to-hand coordination, speed and range of motion (e.g., for hands, feet, elbows, knees, etc.) Differences in times measured for buttons at different heights and radii are useful for characterizing the user's range of motion and peripheral vision.

An important feature of controller 112 is that several sets of test results can be stored and date-stamped so that the therapist or physician can analyze a patient's progress over time by analyzing the trends in reaction time for selected stimuli. The data can be organized by test type and by the specific stimulus presented to the patient.

Figure 4:
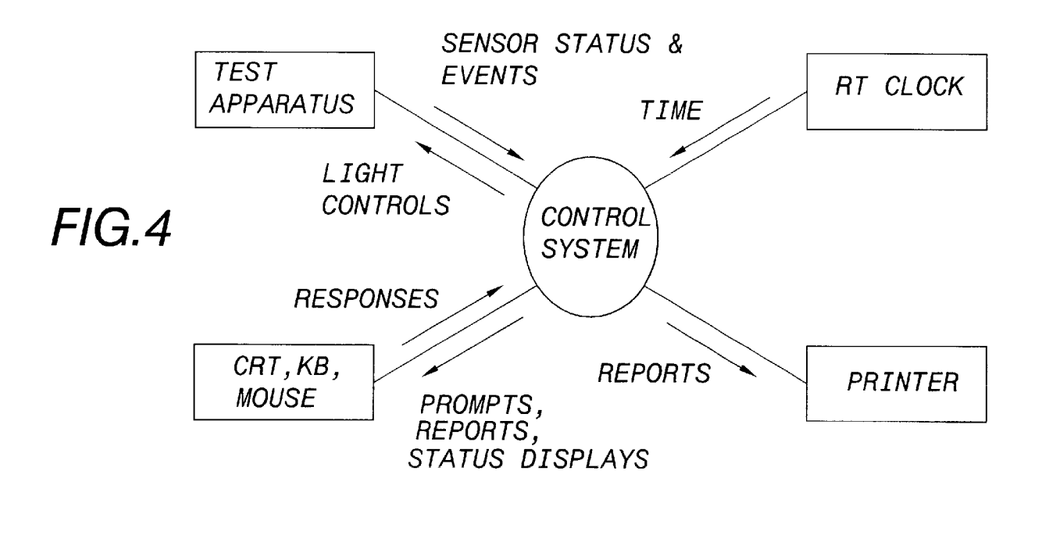
FIG. 4 is a context diagram establishing relationships between elements controlled by the controller software.

The computer or controller used in any of the three embodiments described above includes software for analyzing and displaying the data in any of several formats. FIG. 4 is a context diagram establishing relationships between elements controlled by the controller software. The data can be moved to a spreadsheet or database for storage, plotting and printing. The computer software displays a menu allowing the therapist to either perform a test (or exercise), archive patient histories, or display the patient histories (e.g., on display monitor 136).

Figure 5:
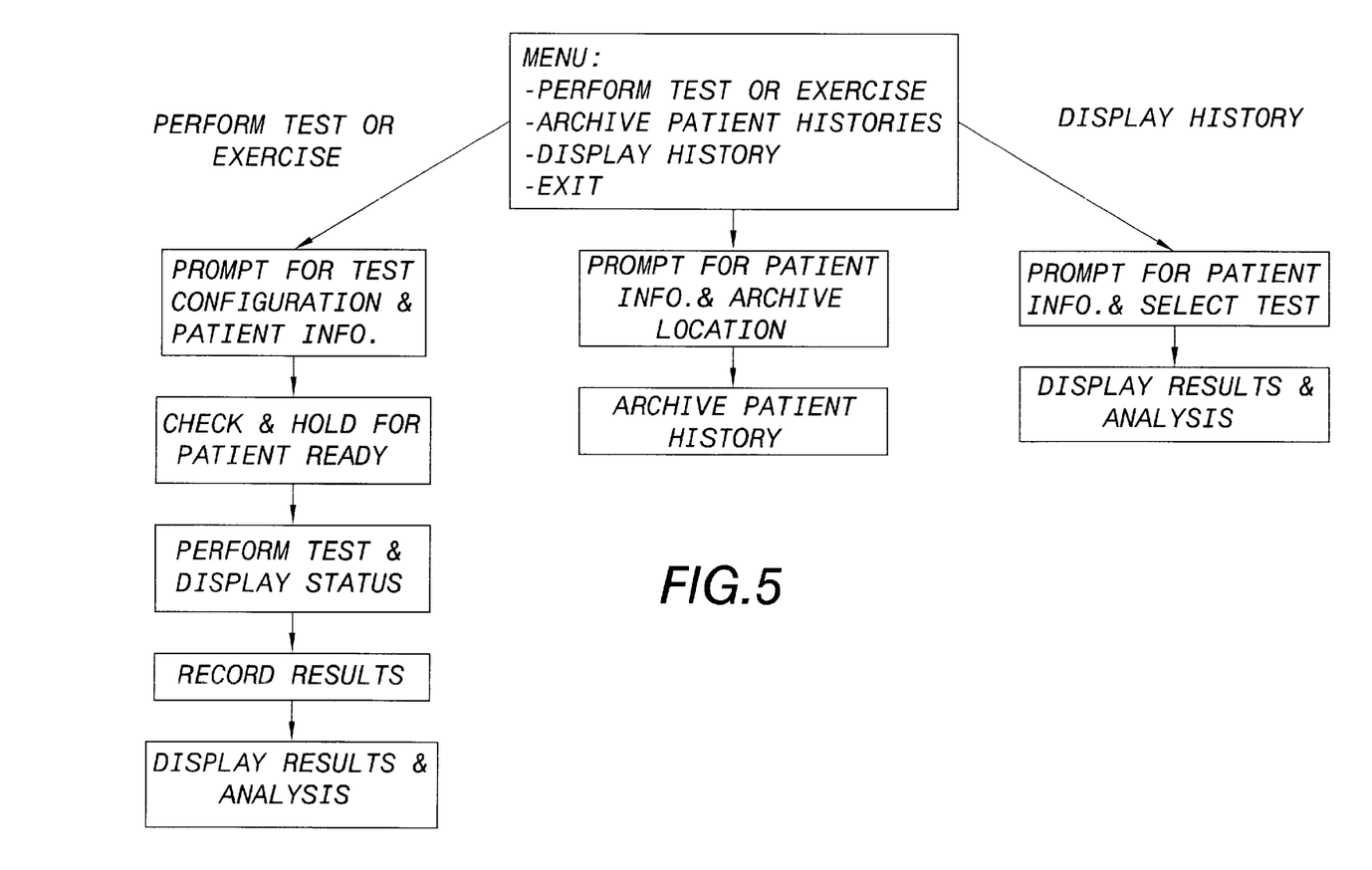
FIG. 5 is a software system flow diagram illustrating the conceptual phases of the operations performed during execution of the controller software.

FIG. 5 is a software system flow diagram illustrating the conceptual phases of the operations performed during execution of the controller software. If performing a test is chosen from an initial menu, the first step is to prompt for test configuration and patient information, then check and hold for patient ready condition, perform the test and display the results, record the results, and display the results with analysis. The initial prompt gives the therapist an opportunity to record information needed to perform the test or exercise and provide identifying information about the patient such as the patient name and other vital information. The therapist also selects whether to use a random sequence of a selected length or a preselected sequence and whether results should be recorded (for a test) or not recorded (for an exercise).

Figure 6:
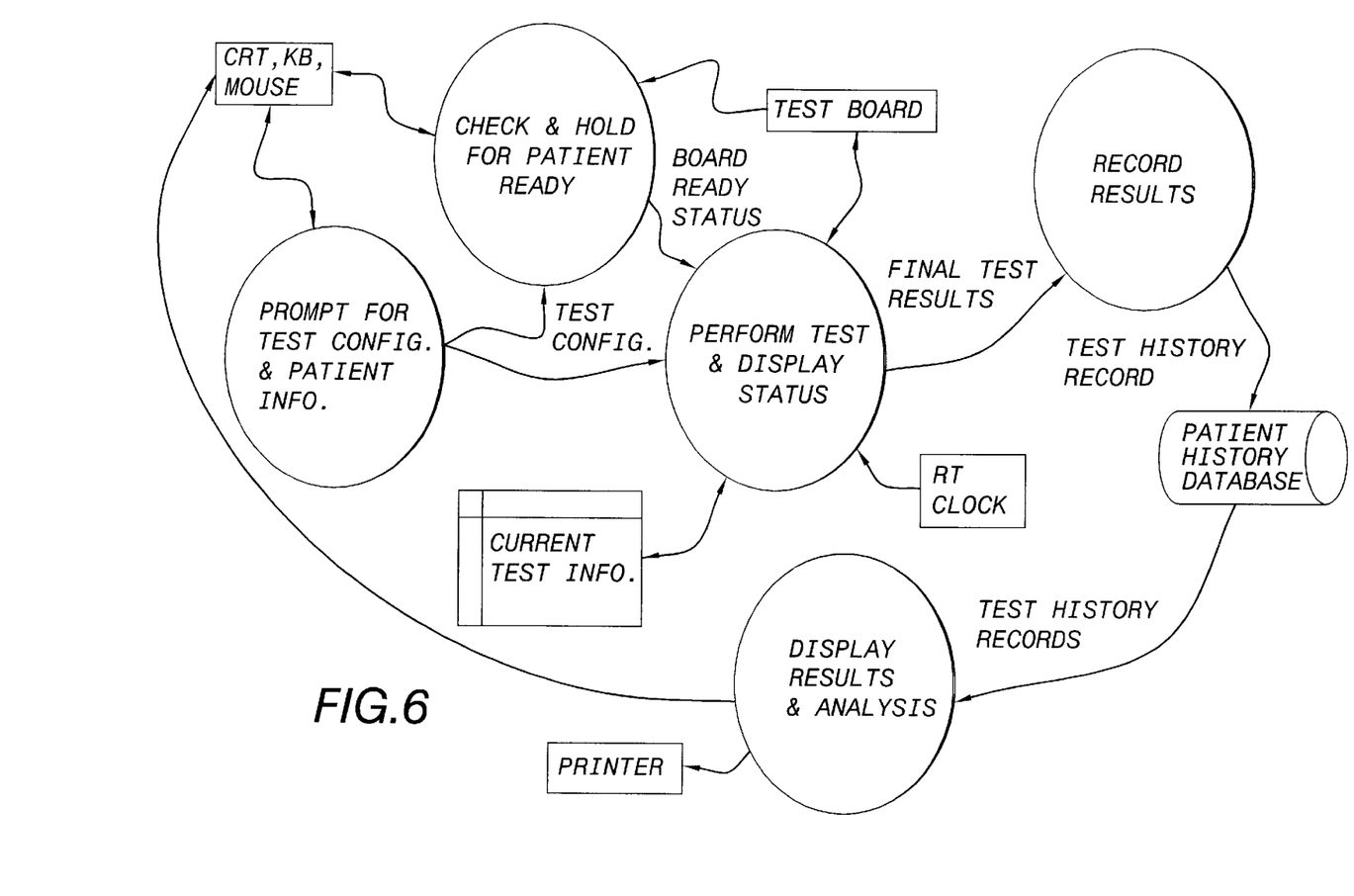
FIG. 6 is a controller software data flow diagram illustrating the flow and storage of information in the "performed test" sequence, the square boxes are external elements called out in the context diagram of FIG. 4.
Figure 7:
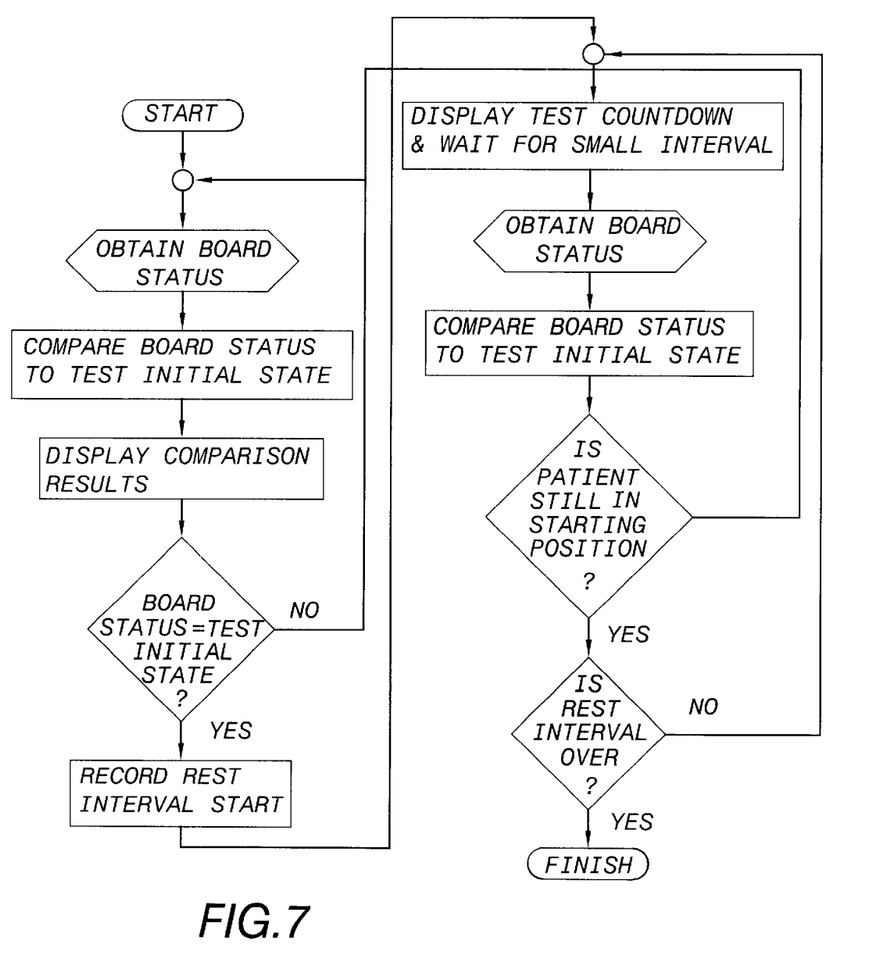
FIG. 7 is a software logic diagram for the "check and hold for patient ready" sequence of steps, as used in conjunction with the finger test system of FIG. 1.
Figure 8:
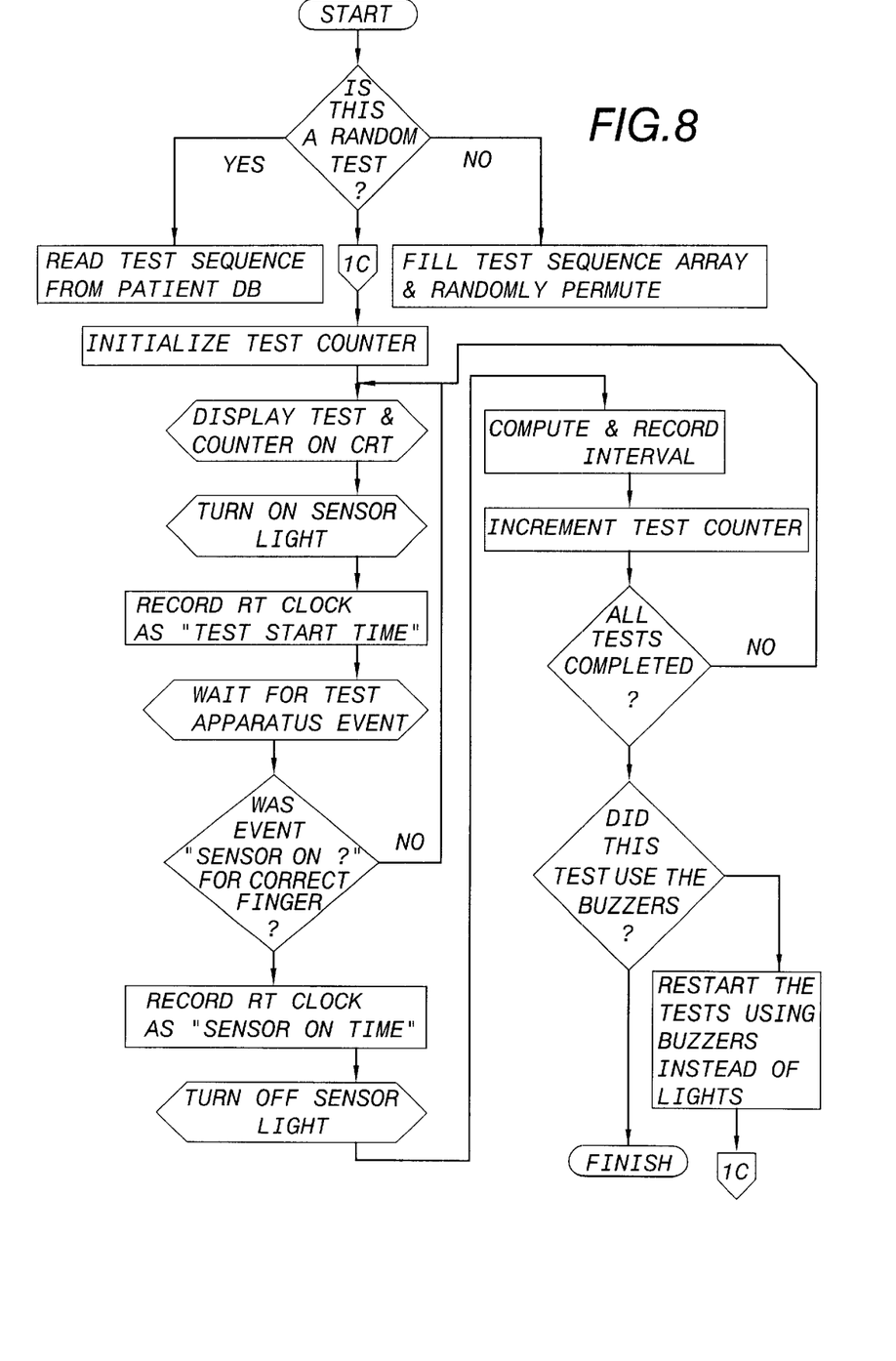
FIG. 8 is a software logic diagram for the "perform test and display" sequence as used in conjunction with the finger test embodiment of FIG. 1.

FIG. 6 is a controller software data flow diagram illustrating the flow and storage of information in the "performed test" sequence, the square boxes are external elements called out in the context diagram of FIG. 4; FIG. 7 is a software logic diagram for the "check and hold for patient ready" sequence of steps, as used in conjunction with the finger test system of FIG. 1; and FIG. 8 is a software logic diagram for the r "perform test and display" sequence as used in conjunction with the finger test embodiment of FIG. 1. Initially, the user or patient must be readied for the test whereby the hand placement is checked and sensors are checked for activation, in sequence. Once the appropriate sensors are activated continuously for a trial period of 10 seconds, the patient is deemed to be ready. In performing the test, the software directs the system to light one of the finger lights and time the interval between the light coming on and the appropriate button being pressed. Once the test sequence is completed using light annunciators, the test is repeated using the vibrotactile buzzer annunciators. If an error occurs during testing (such as the wrong finger button being pressed) the error is recorded along with other test results.

Figure 9:
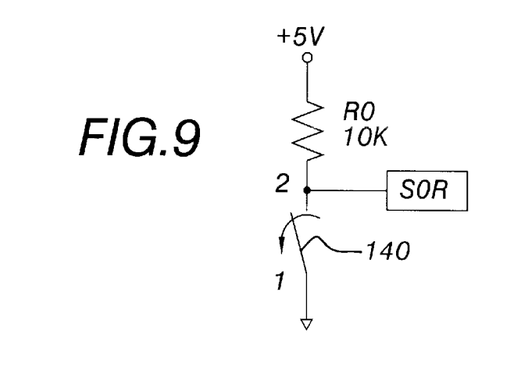
FIG. 9 is an example of the circuits used in the microswitch sensors of the reflex testing system of FIG. 2.
Figure 10:
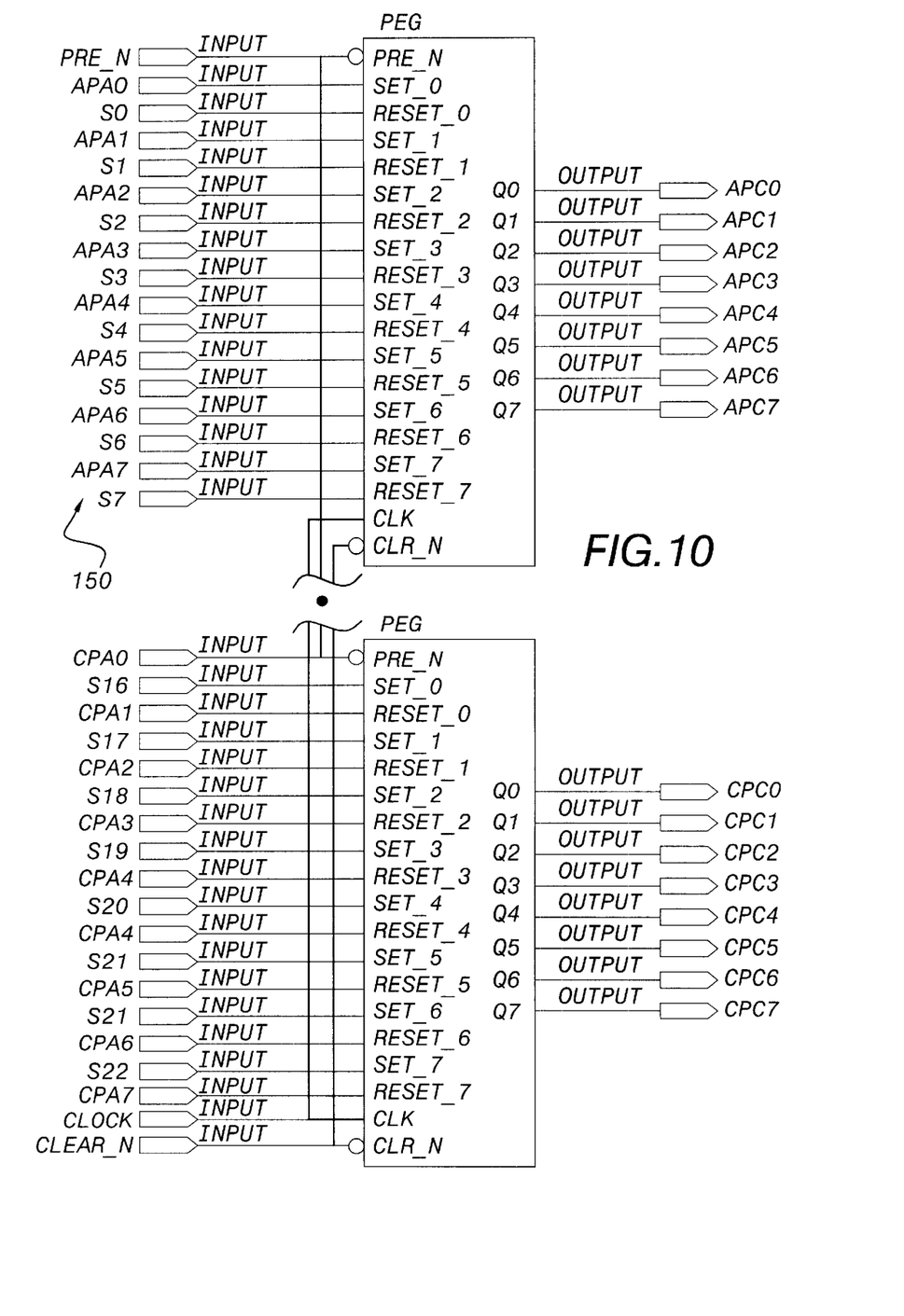
FIG. 10 is a wiring diagram illustrating connections between circuits such as those in FIG. 9 to semiconductor chips having a number of flip flops for generating output signals.
Figure 11:
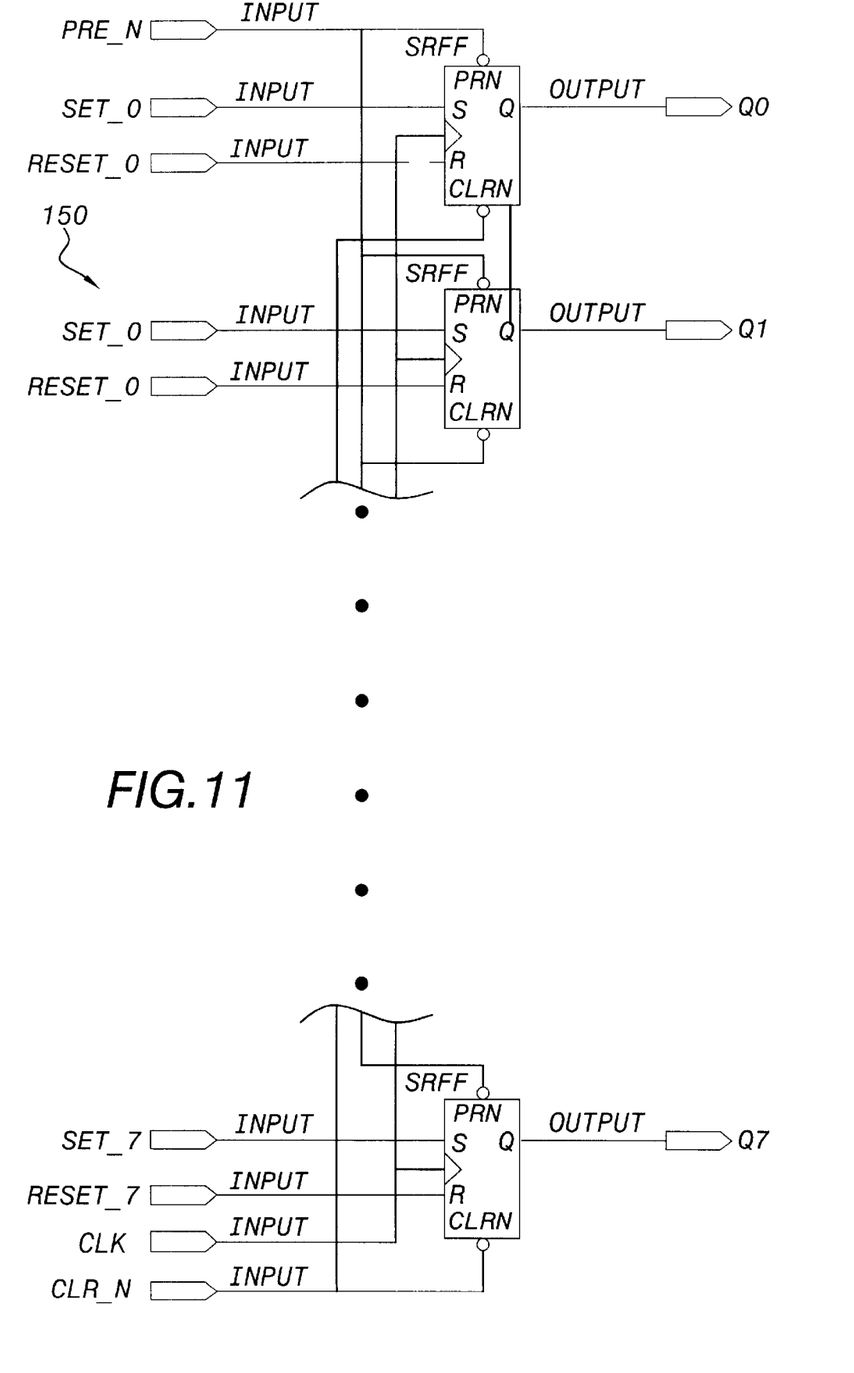
FIG. 11 is a schematic diagram illustrating the wiring between individual flip-flops such as those illustrated in the wiring diagram of FIG. 10.

FIG. 9 is an example of the circuits used in the microswitch sensors of the reflex testing system of FIG. 2; in particular, switch 140 is representative of a sensing microswitch integrated into, for example, reset button 32 in finger subarea 28a of the embodiment of FIG. 1 or, alternatively, a sensing microswitch incorporated into receiving aperture 67 of the peg-board embodiment of FIG. 2, or a sensing microswitch included in button 132 of the hemispherical test system of FIG. 3. The controller (e.g., 74) includes circuitry responsive to each sensing microswitch 140; in particular, FIG. 10 is a wiring diagram illustrating connections between sensing circuits such as those in FIG. 9 to semiconductor chips having a number of flip-flops for generating output signals for transmission to the controller. The SOR connection in FIG. 9 is connected to the input 150 labeled "S0" of FIG. 10. FIG. 11 is a schematic diagram illustrating the wiring between individual flip-flops such as those illustrated in the wiring diagram of FIG. 10; input 150 is identified schematically as "SET_0". The SET and RESET inputs to the flip-flops illustrated in FIGS. 10 and 11 are set to begin a test and reset upon completion. The controller (e.g., 74) provides annunciator driving outputs to start each test and is responsive to the flip-flop circuits to detect and time the passing of each tested event.

From the description provided, it will be appreciated by those skilled in the art that the present invention makes available a response measuring system for measuring the time required for a user or patient to respond to a prompting, annunciated event, including a controller with at least first and second annunciator driving outputs, first and second sensor input receiving circuits, a timer responsive to the annunciator driving outputs and the sensor input receivers and a memory responsive to the sensor input receivers. The response measuring system also includes a first annunciator responsive to the controller first annunciator driving output, a second annunciator responsive to the controller second annunciator driving output, a first sensor connected to a sensor input signal generator generating a first sensor input signal for transmission to the controller first sensor input receiver, a second sensor connected to a sensor input signal generator generating a second sensor input signal for transmission to the controller second sensor input receiver, a support member or housing carrying the first annunciator, the second annunciator, the first sensor and the second sensor; where the annunciators are positioned to be perceivable (e.g., seen or felt) by the user, and where the controller timer is configured to measure time elapsed between actuation of the first annunciator and generation of the first sensor input signal, and generate a response time signal from the elapsed time, and where the controller memory is configured to store and, optionally, display the elapsed time.

Of course, many trivial substitutions are possible, sensing micro-switches need not be used for sensing the position of a peg or depression by a user, thermal sensors, optical sensors, or capacitive sensors or pressure sensors may be employed, instead. Similarly, LEDs need not be used to provide visual prompting of the user, instead, incandescent bulbs, fluorescent lamps, plasma display elements or Liquid Crystal Display (LCD) display elements may be used to provide a visible annunciator to prompt the user.

In as much as the present invention is subject to various modifications and changes in detail, the above description of preferred embodiments is intended to be exemplary only and not limiting. It is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A response measuring system for measuring the time required for a user to respond to a prompting event, comprising:

a controller; said controller including first and second annunciator driving outputs, first and second sensor input receivers, a timer responsive to said annunciator driving outputs and said sensor input receivers and a memory responsive to said sensor input receivers;

a first annunciator responsive to said controller first annunciator driving output;

a second annunciator responsive to said controller second annunciator driving output;

a first sensor connected to a sensor input signal generator generating a first sensor input signal transmitted to said controller first sensor input receiver;

a second sensor connected to a sensor input signal generator generating a second sensor input signal transmitted to said controller second sensor input receiver;

a support member carrying said first annunciator, said second annunciator, said first sensor and said second sensor, wherein said annunciators are positioned to be perceivable by the user;

said controller timer being configured to measure time elapsed between actuation of said first annunciator and generation of said first sensor input signal, and generate a response time signal from said elapsed time;

wherein said memory is configured to store said elapsed time; and wherein said support member includes a housing with a first area configured to receive a first hand with fingers and thumb pressed against the first area.

2. The response measuring system of claim 1, wherein said support member includes a housing with a second area configured to receive a second hand opposite said first hand, with fingers and thumb pressed against the second area.

3. A response measuring system for measuring the time required for a user to respond to a prompting event, comprising:

a controller; said controller including first and second annunciator driving outputs, first and second sensor input receivers; a timer responsive to said annunciator driving outputs and said sensor input receivers and a memory responsive to said sensor input receivers;

a first annunciator responsive to said controller first annunciator driving output;

a second annunciator responsive to said controller second annunciator driving output;

a first sensor connected to a sensor input signal generator generating a first sensor input signal transmitted to said controller first sensor input receiver;

a second sensor connected to a sensor input signal generator generating a second sensor input signal transmitted to said controller second sensor input receiver;

a support member carrying said first annunciator, said second annunciator, said first sensor and said second sensor, wherein said annunciators are positioned to be perceivable by the user;

said controller timer being configured to measure time elapsed between actuation of said first annunciator and generation of said first sensor input signal, and generate a response time signal from said elapsed time;

wherein said memory is configured to store said elapsed time;

wherein said support member includes a housing configured as a partial spherical interior surface;

said annunciators and sensors being arranged on said partial spherical interior surface.

4. A response measuring system for measuring the time required for a user to respond to a prompting event, comprising:

a controller; said controller including first and second annunciator driving outputs, first and second and third sensor input receivers; a timer responsive to said annunciator driving outputs and said sensor input receivers and a memory responsive to said sensor input receivers;

a first annunciator responsive to said controller first annunciator driving output;

a second annunciator responsive to said controller second annunciator driving output;

a first sensor connected to a sensor input signal generator generating a first sensor input signal transmitted to said controller first sensor input receiver;

a second sensor connected to a sensor input signal generator generating a second sensor input signal transmitted to said controller second sensor input receiver;

a support member carrying said first annunciator, said second annunciator, said first sensor and said second sensor, wherein said annunciators are positioned to be perceivable by the user;

said controller timer being configured to measure time elapsed between actuation of said first annunciator and generation of said first sensor input signal, and generate a response time signal from said elapsed time;

wherein said memory is configured to store said elapsed time; and wherein said support member includes a housing having a substantially hemispherical interior surface carrying said annunciators and sensors.

5. The response measuring system of claim 4, further including a central actuator button including a third sensor connected to a sensor input signal generator generating a third sensor input signal transmitted to said controller third sensor input receiver;

said central actuator button being disposed in the center of said substantially hemispherical interior surface;

said first annunciator and said first sensor being incorporated into a first lighted press button incorporating an electrical switch; said second annunciator and said second sensor being incorporated into a second lighted press button incorporating an electrical switch; and said first and second lighted press buttons being disposed on said substantially hemispherical interior surface;

said controller timer being configured to measure time elapsed between actuation of said first annunciator and generation of said third sensor input signal, and generate a response time signal from said elapsed time.

6. The response measuring system of claim 5, said central actuator button, said first lighted press button and said second lighted press button being disposed in a linear array aligned along a radial line within said substantially hemispherical interior surface.

7. The response measuring system of claim 6, further including third and fourth lighted press buttons disposed in a second linear array aligned along a second radial line within said substantially hemispherical interior surface and radially spaced from said first and second lighted press buttons.

8. The response measuring system of claim 7, said substantially hemispherical interior surface including a test position proximate the center of the hemisphere at a bottom edge; and being situated to facilitate use by a standing user.

9. The response measuring system of claim 7, said substantially hemispherical interior surface test position including designated positions for left and right feet disposed directly in front of said central actuator button.

10. A response measuring system for measuring the time required for a user to respond to a prompting event, comprising:

a controller; said controller including a plurality of annunciating member driving outputs, a plurality of sensing member input receivers, a timer responsive to said annunciating member driving outputs and said sensing member input receivers and a memory;

a plurality of annunciating members, wherein each annunciating member is independently controlled by said controller via a corresponding annunciating member driving output;

a plurality of sensing members, wherein each sensing member is independently connected to said controller via a corresponding sensing member input receiver to transmit a sensing input signal to said controller upon actuation of the sensing member by the user; and a support member carrying said annunciating members and said sensing members, wherein said annunciating members are positioned to be perceivable by the user;

wherein said controller timer is configured to measure time elapsed between actuation of at least one annunciating member and transmission of at least one sensing input signal by at least one corresponding sensing member to generate a response time signal from the elapsed time;

wherein said memory is configured to receive the response time signal generated from said controller timer and store the elapsed time; and wherein at least a portion of said sensing members are disposed on said support member so as to align with each finger and thumb of at least one hand of the user when placed upon said support member to thereby facilitate the actuation of a single sensing member by the user's finger or thumb in response to actuation of a corresponding annunciating member.

* * * * *